United States Patent [19]

Suyama et al.

[11] Patent Number: 5,446,191

[45] Date of Patent: Aug. 29, 1995

[54] 1-CYCLOHEXYL-1-METHYLETHYL-PEROXY CARBONATE, METHOD FOR PRODUCTION THEREOF, AND USES THEREFOR

[75] Inventors: Shuji Suyama; Tooru Nishikawa; Masaru Matsushima, all of Aichi; Hiroshi Okada, Tokoname, all of Japan

[73] Assignee: NOF Corporation, Tokyo, Japan

[21] Appl. No.: 190,459

[22] Filed: Feb. 2, 1994

[30] Foreign Application Priority Data

Feb. 2, 1993 [JP] Japan ................... 5-036248

[51] Int. Cl.$^6$ ................................ C07C 69/74
[52] U.S. Cl. ....................... 560/126; 525/383; 525/387
[58] Field of Search .......................... 560/126

[56] References Cited

U.S. PATENT DOCUMENTS

| | | |
|---|---|---|
| 2,374,789 | 5/1945 | Strain . |
| 3,082,236 | 3/1963 | Mageli et al. . |
| 5,117,047 | 5/1992 | Suyama et al. . |
| 5,258,465 | 11/1993 | Suyama et al. . |
| 5,292,914 | 3/1994 | Suyama et al. . |

FOREIGN PATENT DOCUMENTS

| | | |
|---|---|---|
| 0478214 | 4/1992 | European Pat. Off. . |
| 52-31255 | 8/1977 | Japan . |
| 62-43409 | 2/1987 | Japan . |
| 62-246908 | 10/1987 | Japan . |

OTHER PUBLICATIONS

CA Abstract 118:235262, Ujigawa, et al., Nov. 1992.
CA. Registry No. 97574-84-0, Beilstein, prior to 1967.

*Primary Examiner*—Bernard Lipman
*Attorney, Agent, or Firm*—Oblon, Spivak, McClelland, Maier & Neustadt

[57] ABSTRACT

A 1-cyclohexyl-1-methylethylperoxy carbonate represented by the formula:

$$\left( H_2C \begin{array}{c} H_2C-CH_2 \\ H_2C-CH_2 \end{array} CH-\underset{\underset{CH_3}{|}}{\overset{\overset{CH_3}{|}}{C}}-OO-\overset{\overset{O}{\|}}{C}-O \right)_{n_1} R_1$$

(wherein $n_1$ stands for 1 or 2 and, when $n_1$ is 1, $R_1$ stands for an alkyl group of up to 14 carbon atoms, an aralkyl group of up to 14 carbon atoms, an alkoxyalkyl group of up to 14 carbon atoms, a cycloalkyl group of up to 14 carbon atoms, or an aryl group of up to 14 carbon atoms, and when $n_1$ is 2, $R_1$ stands for an alkylene group of up to 16 carbon atoms, an aralkylene group of up to 16 carbon atoms, an oxaalkylene group of up to 16 carbon atoms, a cycloalkylene group of up to 16 carbon atoms, or a phenylene group of up to 16 carbon atoms) is a novel compound. It is produced by causing a chloroformate represented by the formula:

$$R_2 \left( O-\overset{\overset{O}{\|}}{C}-Cl \right)_{n_2}$$

(wherein $n_2$ has the same meaning as $n_1$ in the preceding formula) to react with 1-cyclohexyl-1-methylethylhydroperoxide. It is useful as a polymerization initiator for a vinyl monomer, a curing agent for an unsaturated polyester resin and a cross-linking agent for a polymer.

8 Claims, No Drawings

1-CYCLOHEXYL-1-METHYLETHYLPEROXY CARBONATE, METHOD FOR PRODUCTION THEREOF, AND USES THEREFOR

BACKGROUND OF THE INVENTION

1. Field of the Invention

This invention relates to a novel peroxy carbonate, a method for the production thereof, and uses therefor.

2. Prior Art Statement

It is known to use dialkyl peroxides such as dicumyl peroxide, peroxy ketals such as 1,1-bis(t-butylperoxy)-3,3,5-trimethyl cyclohexane, and peroxy esters such as t-butyl-peroxyisopropyl carbonate and t-butylperoxy benzoate, all of which are organic peroxides active at medium to high temperatures, as polymerization initiators, cross-linking agents, and curing agents (as disclosed in Japanese Patent Public Disclosure SHO 62(1987)-246908, Japanese Patent Publication SHO 52(1977)31255 and Japanese Patent Public Disclosure SHO 62(1987)43409).

Notwithstanding, from the practical viewpoint, there continues to be a need for polymerization initiators, cross-linking agents, and curing agents that are of higher quality than these known compounds.

SUMMARY OF THE INVENTION

Through a long-term study, the present inventors have been ascertained that 1-cyclohexyl-1-methylethylperoxy carbonate, a novel compound not yet reported in the literature, satisfies this need. This invention has been accomplished as a result.

To be specific, this invention is directed to 1-cyclohexyl-1-methylethylperoxy carbonate represented by the formula:

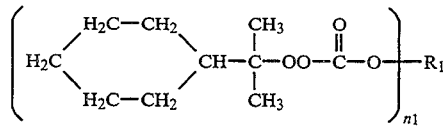

(wherein $n_1$ stands for 1 or 2 and, when $n_1$ is 1, $R_1$ stands for an alkyl group of up to 14 carbon atoms, an aralkyl group of up to 14 carbon atoms, an alkoxyalkyl group of up to 14 carbon atoms, a cycloalkyl group of up to 14 carbon atoms,, or an aryl group of up to 14 carbon atoms, and when $n_1$ is 2, $R_1$ stands for an alkylene group of up to 16 carbon atoms, an aralkylene group of up to 16 carbon atoms, an oxaalkylene group of up to 16 carbon atoms, a cycloalkylene group of up to 16 carbon atoms, or a phenylene group of up to 16 carbon atoms), a method for the production of this compound, and the use of the compound as a polymerization initiator for a vinyl monomer, a curing agent for an unsaturated polyester resin, and a cross-linking agent for a polymer.

The 1-cyclohexyl-1-methylethylperoxy carbonate of this invention (hereinafter referred to simply as the "peroxy carbonate of this invention"), as shown above, has a structure possessing methyl groups and a cyclohexyl group attached to the carbon atom having a peroxy group coupled therewith α-position carbon). It is a novel compound not yet reported in the literature.

The upper limit of the number of carbon atoms of the substituent $R_1$ in the formula shown above is decided with consideration to the practical utility of the novel compound. The alkyl group or alkylene group may be in a linear form or a branched form.

DESCRIPTION OF THE PREFERRED EMBODIMENTS

As concrete examples of the peroxy carbonate of this invention, 1-cyclohexyl-1-methylethylperoxyisopropyl carbonate, 1-cyclohexyl-1-methylethylperoxy-sec-butyl carbonate, 1-cyclohexyl-1-methylethylperoxy-2-ethylhexyl carbonate, 1-cyclohexyl-1-methylethylperoxycyclododecyl carbonate, 1-cyclohexyl-1-methylethylperoxy-2-methoxybutyl carbonate, 1-cyclohexyl-1-methylethylperoxy-p-tolyl carbonate, and 1,6-bis(1-cyclohexyl-1-methylethylperoxy)hexamethylene dicarbonate may be cited.

The peroxy carbonates of this invention can be classified into monoperoxy carbonates (n=1) and diperoxy carbonates (n=2).

The method for the production of a peroxy carbonate of this invention will now be described.

Specifically, this production is attained by causing chloroformate represented by the formula:

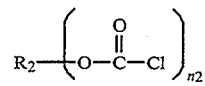

(wherein $n_2$ stands for 1 or 2 and, when $n_2$ is 1, $R_2$ stands for an alkyl group of up to 14, carbon atoms, an aralkyl group of up to 14 carbon atoms, an alkoxyalkyl group of up to 14 carbon atoms, a cycloalkyl group of up to 14 carbon atoms, or an aryl group of up to 14 carbon atoms, and when $n_2$ is 2, $R_2$ stands for an alkylene group of up to 16 carbon atoms, an aralkylene group of up to 16 carbon atoms, an oxaalkylene group of up to 16 carbon atoms, a cycloalkylene group of up to 16 carbon atoms, or a phenylene group of up to 16 carbon atoms) to react with 1-cyclohexyl-1-methylethylhydroperoxide in the presence of an alkali compound or a tertiary amine at a temperature lower than the decomposition temperature of the peroxy carbonate to be produced.

As concrete examples of the alkali compound mentioned above, such inorganic bases as NaOH, KOH, LiOH, and NaCO$_3$ may be cited. As concrete examples of the tertiary amine mentioned above, pyridine, triethyl amine, and tributyl amine may be cited.

A solvent may be used for the reaction mentioned above. The use of a solvent in the reaction reduces the reaction time and improves the yield.

Solvents preferably used for the reaction include aromatic hydrocarbons (such as toluene and ethyl benzene), aliphatic hydrocarbons (such as hexane, octane, petroleum naphtha, and mineral spirit), and aliphatic hydrocarbons having isoparaffin as a main component (such as a product of Shell Chemical Co., Ltd. marketed under the tradename "Shell Sol").

The molar ratio of chloroformate to 1-cyclohexyl-1-methylethylhydroperoxide in the reaction mentioned above is in the range of 1:0.8 to 1:1.4. When the molar ratio deviates from this range, the product is deficient in quality and yield.

The reaction temperature is not higher than the temperature of decomposition of the peroxy carbonate to be synthesized. It is generally in the approximate range of −10° C. to +40° C.

The chloroformate used in this invention can be produced by the reaction of a monohydric or dihydric alcohol with phosgene.

As concrete examples of the monohydric alcohol, ethyl alcohol, n-propyl alcohol, isopropyl alcohol, n-butyl alcohol, sec-butyl alcohol, t-butyl alcohol, cumyl alcohol, 2-ethylhexyl alcohol, cyclohexyl alcohol, cyclododecyl alcohol, 2-methoxybutyl alcohol, phenol, and p-methyl phenol may be cited.

As concrete examples of the dihydric alcohol, ethylene glycol, propylene glycol, 1,6-hexane diol, triethylene glycol, 1,2-butane diol, 2-butene-1,4-diol, and 2,2-di(4-hydroxycyclohexyl)-propane may be cited.

The 1-cyclohexyl-1-methylethylhydroperoxide used in the preparation of the peroxy carbonate of this invention is represented by the following structural formula:

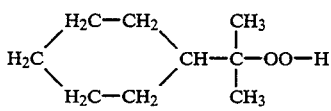

This hydroperoxide can be prepared by treating 2-cyclohexyl-2-propanol (hexahydro-α-cumyl alcohol) with an excess amount of hydrogen peroxide in the presence of a strong acid catalyst such as sulfuric acid, phosphoric acid, or perchloric acid, the acid form of an ion-exchange resin, or p-toluene-sulfonic acid.

The hydroperoxide is a colorless transparent liquid. The identity and the chemical structure of this compound are confirmed by the infrared absorption spectrum and the nuclear magnetic resonance spectrum. The peroxy group content of this compound can be determined in accordance with the active oxygen content which is determined by iodometry.

As in the case of the hydroperoxide, the structure of the peroxy carbonate of this invention is determined by the infrared absorption spectrum and the nuclear magnetic resonance spectrum.

The peroxy carbonate of this invention is possessed of excellent qualities that make the compound useful as a polymerization initiator for a vinyl monomer, a curing agent for an unsaturated polyester resin, and a cross-linking agent for a polymer.

Use as a polymerization initiator for a vinyl monomer:

The peroxy carbonate of this invention is an effective polymerization initiator in the polymerization or copolymerization of a vinyl monomer. As concrete examples of the vinyl monomer for which the peroxy carbonate of this invention can be effectively used there can be mentioned olefins such as ethylene, propylene, styrene, α-methyl styrene and chlorostyrene, diolefins such as 1,3-butadiene, isoprene, and chloroprene, vinyl esters such as vinyl acetate and vinyl propionate, unsaturated nitriles such as acrylonitrile and methacrylonitrile, acrylic acid and methacrylic acid and esters and amides thereof, vinyl halides and vinylidene halides such as vinyl chloride, vinyl bromide, vinyl fluoride, vinylidene chloride and vinylidene fluoride, perhaloolefins such as ethylene tetrafluoride, vinyl ethers such as methyl vinyl ether and butyl vinyl ether, and mixtures thereof such as styrene-butadiene and acrylonitrile-butadiene-styrene.

The amount of the peroxy carbonate of this invention used as a polymerization initiator for a vinyl monomer is in the range of 0.001 to 1 part by weight, preferably 0.01 to 0.5 part by weight, as a pure compound based on 100 parts by weight of the vinyl monomer used for polymerization. The temperature of polymerization is in the range of 20° C. to 250° C., preferably 30° C. to 200° C.

The peroxy carbonate of this invention may be used either singly or in combination with another polymerization initiator. The other polymerization initiator used in addition to the peroxy carbonate may be selected from among the conventional polymerization initiators, depending on such factors as the polymerization temperature. The amount of the other polymerization initiator may be properly decided to suit the desired polymerization velocity and the physical properties of the produced polymer.

Use as curing agent for unsaturated polyester resin:

The peroxy carbonate of this invention has excellent qualities that make the compound useful as a curing agent for an unsaturated polyester resin.

The unsaturated polyester resins which can be cured using the peroxy carbonate of this invention as a curing agent generally contain an unsaturated polyester and at least one vinyl monomer.

As concrete examples of the unsaturated polyester, there can be mentioned such polyesters as are obtained by esterifying at least one ethylenically unsaturated di- or poly-carboxylic acid, acid anhydride, or acid halide such as, for example, maleic acid, fumaric acid, glutaric acid, phthalic acid, itaconic acid, terephthalic acid, or tetrahydrophthalic acid with a saturated or unsaturated di- or poly-ol such as, for example, ethylene glycol, diethylene glycol, triethylene glycol, 1,2- or 1,3-propane diol, 1,2-butane diol, 2-butene-1,4-diol, or glycerin.

As concrete examples of the vinyl monomer which is the other component of the unsaturated polyester resin composition, styrene, vinyl toluene, α-methyl styrene, diallyl phthalate, acrylonitrile, methyl methacrylate, and mixtures thereof which are copolymerizable with the polyester mentioned above may be cited.

The amount of the peroxy carbonate of this invention used as a curing agent is generally in the range of 0.1 to 3 parts by weight, preferably 0.5 to 2 parts by weight, based on 100 parts by weight of the unsaturated polyester resin. The curing temperature in this case is in the range of about 20° to 200° C.

Use as a cross-linking agent for polymer:

The peroxy carbonate of this invention has excellent qualities that make it useful as a cross-linking agent for a polymer.

As concrete examples of polymers which can be cross-linked using the peroxy carbonate of this invention as a cross-linking agent there can be mentioned such elastomers as natural rubber, butadiene rubber, isoprene rubber, silicone rubber, ethylene-propylene rubber, ethylene-propylene-ethylidene norbornene rubber, and styrene-butadiene rubber and such thermoplastic compounds as polyethylene and polyethylene-vinyl acetate copolymer.

The amount of the peroxy carbonate of this invention used as a cross-linking agent is generally in the range of 0.3 to 10 parts by weight, preferably 1 to 5 parts by weight, based on 100 parts by weight of the polymer under treatment.

The cross-linking reaction is carried out under a pressure in the range of 50 to 200 kg/cm² at a temperature in the range of about 100° to 200° C.

The peroxy carbonate of this invention is used in its form as synthesized, but, if necessary, can be suitably diluted.

The 1-cyclohexyl-1-methylethylperoxy carbonate of this invention is a novel compound that exhibits high activity when it is used as a polymerization initiator, a cross-linking agent, or a curing agent as described above.

This invention will now be described more specifically with reference to working examples and comparative experiments.

REFERENCE EXAMPLE (Synthesis of 1-cyclohexyl-1-methylethylhydroperoxide)

In a four-neck flask having an inner volume of 500 ml and provided with a stirrer, 85.1 g of an aqueous 50% hydrogen peroxide solution was placed and stirred and 60.1 g of 98% sulfuric acid was added dropwise to the stirred aqueous solution at an inner temperature of not higher than 10° C. Then, 73.5 g of 96.8% 2-cyclohexyl-2-propanol was added dropwise to the stirred mixture with the inner temperature of the flask kept in the range of 5° to 10° C. The resultant reaction mixture was continuously stirred at the same temperature for two hours and 30 minutes. The water phase was separated. The remaining oil phase was neutralized with an aqueous 5% sodium bicarbonate solution, washed, and washed twice more with water. The washed reaction product was dried over anhydrous magnesium sulfate, to obtain 69.6 g of a colorless transparent liquid. This liquid was found to have an active oxygen content of 9.60%. The calculation using this numerical value shows that the product had a purity of 95.0% and a yield of 83.5 mol %.

This substance was identified by the IR and NMR spectra.

IR spectrum: 0-0 stretching vibration 860 cm$^{-1}$ 00-H stretching vibration 3,370 cm$^{-1}$ NMR spectrum (CDCL$_3$)

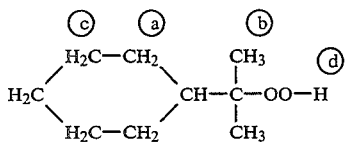

| | | | |
|---|---|---|---|
| H ⓐ: | δ0.86 ~ 1.33, | m, | 5H |
| H ⓑ: | δ1.10, | s, | 6H |
| H ⓒ: | δ1.49 ~ 1.86, | m, | 6H |
| H ⓓ: | δ9.64, | s, | 1H |

EXAMPLE 1

(Synthesis of 1-cyclohexyl-1-methylethylperoxy isopropyl carbonate)

In a four-neck flask having an inner volume of 20 ml and provided with a stirrer, 42.1 g of an aqueous 20% potassium hydroxide solution and 10 g of hexane were placed and stirred, and 16.7 g of the 95.0% 1-cyclohexyl-1-methylethylhydroperoxide synthesized in the Reference Example was added to the stirred mixture with the liquid temperature kept at 15° C. The resultant mixture was continuously stirred and 14.1 g of isopropyl chloroformate was added dropwise to the stirred mixture over a period of 10 minutes with the liquid temperature kept in the range of 0° to 5° C. The produced mixture was continuously stirred at the same temperature for 30 minutes. The stirred mixture and 20 g of cold water added thereto were together stirred for five minutes continuously. The water phase was separated. The remaining oil phase was washed with 20 g of an aqueous 5% sodium hydroxide solution and then washed three times with water. The solution consequently obtained was dried over anhydrous magnesium sulfate and subjected to vacuum distillation to expel the hexane. As a result, 18.9 g of a colorless transparent liquid was produced. This liquid was found to have an active oxygen content of 6.26%. The calculation using this numerical value shows that the product had a purity of 95.6% and a yield of 73.9 mol %.

The product was identified by the IR and NMR spectra.

IR spectrum: 0-0 stretching vibration 860 cm$^{-1}$ C=0 stretching vibration 1,790 cm$^{-1}$ NMR spectrum (CDCL$_3$)

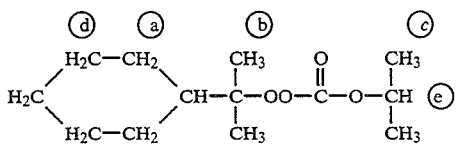

| | | | |
|---|---|---|---|
| H ⓐ: | δ0.90 ~ 1.16, | m, | 5H |
| H ⓑ: | δ1.23, | s, | 6H |
| H ⓒ: | δ1.33, | d, | 6H |
| H ⓓ: | δ1.61 ~ 1.88, | m, | 6H |
| H ⓔ: | δ4.90 ~ 4.99, | m, | 1H |

The product was subjected to a thermal decomposition test using cumene as a solvent (concentration: 0.1 mol/liter). As a result, the 10-hour half-life temperature of this peroxy carbonate was found to be 82.8° C.

EXAMPLES 2 TO 7

(Synthesis of other 1-cyclohexyl-1-methylethylperoxy carbonates)

The procedure of Example 1 was repeated, except that the kind and amount of chloroformate were varied as shown in Table 1. The products consequently obtained were all colorless liquids. The liquids were identified in the same manner as in Example 1. These compounds were tested for 10-hour half-life temperature in the same manner as in Example 1. The results are shown in Table 2.

TABLE 1

| Example No. | Kind of chloroformate | Amount added (g) |
|---|---|---|
| 2 | Sec-butyl chloroformate | 15.7 |
| 3 | 2-Ethylhexyl chloroformate | 22.2 |
| 4 | Cyclododecyl chloroformate | 28.4 |
| 5 | p-Tolyl chloroformate | 19.6 |
| 6 | 2-Methoxybutyl chloroformate | 17.3 |
| 7 | 1,6-Hexane bis-chloroformate | 14.0 |

TABLE 2

| Example No. | Name of compound | T$_{10}$ (°C.) | Purity (%) | Yield (%) |
|---|---|---|---|---|
| 2 | 1-Cyclohexyl-1-methylethylperoxy-sec-butyl carbonate | 81.5 | 95.8 | 70.1 |
| 3 | 1-Cyclohexyl-1-methylethylperoxy-2-ethylhexyl carbonate | 83.2 | 94.1 | 72.5 |
| 4 | 1-Cyclohexyl-1-methylethylperoxycyclododecyl carbonate | 83.1 | 90.4 | 73.1 |

TABLE 2-continued

| Example No. | Name of compound | $T_{10}$ (°C.) | Purity (%) | Yield (%) |
|---|---|---|---|---|
| 5 | 1-Cyclohexyl-1-methyl-ethylperoxy-p-tolyl carbonate | 81.2 | 93.5 | 51.8 |
| 6 | 1-Cyclohexyl-1-methyl-ethylperoxy-2-methoxy-butyl carbonate | 83.0 | 94.2 | 71.7 |
| 7 | 1,6-Bis(1-cyclohexyl-1-methylethylperoxy)-hexamethylene dicarbonate | 83.1 | 94.1 | 75.3 |

(Use as polymerization initiator)

EXAMPLE 8

(Polymerization of styrene)

A glass ampoule having an inner volume of 20 ml was charged with 10 ml of a sample solution obtained by dissolving 0.01 mol of 1-cyclohexyl-1-methylethylperoxyisopropyl carbonate as a polymerization initiator in 1 liter of styrene, evacuated of the entrapped air, and then sealed by fusion. The ampoule was placed in a constant temperature oil bath at 90° C. and left standing therein for four hours to effect polymerization of the styrene. Then, the reaction product was removed from the ampoule, dissolved in benzene, and analyzed by the inner standard method using gas chromatography to determine the unreacted monomer content and the conversion of polymerization. As a result, the conversion of polymerization was found to be 70.5%. The weight average molecular weight of the produced polymer determined by gel permeation chromatography (GPC) was 489,000.

EXAMPLE 9

(Polymerization of styrene)

Bulk polymerization of styrene was carried out by following the procedure of Example 8 while using 1-cyclohexyl-1-methylethylperoxy-2-ethylhexyl carbonate instead as a polymerization initiator. The conversion of the polymerization was found to be 68.8% and the weight average molecular weight of the produced polymer to be 476,000.

COMPARATIVE EXPERIMENT 1

(Polymerization of styrene)

Polymerization of styrene was carried out by following the procedure of Example 9 while using t-butyl-peroxyisopropyl carbonate instead as a polymerization initiator. As a result, the conversion of the polymerization was found to be 62.8% and the weight average molecular weight to be 610,000.

A comparison of the results of Examples 8 and 9 with those of Comparative Experiment 1 shows that the peroxides of the present invention were better in polymerization activity the conventional peroxide of Comparative Experiment 1.

EXAMPLE 10

(Polymerization of MMA)

A glass ampoule having an inner volume of 20 ml was charged with 10 ml of a sample solution obtained by dissolving 0.001 mol of 1-cyclohexyl-1-methylethylperoxyisopropyl carbonate and 1 g of n-dodecyl mercaptan in 1 liter of methyl methacrylate, evacuated of the entrapped air, and sealed by fusion. This ampoule was left standing at 100° C. for four hours to effect polymerization of the methyl methacrylate. The product was tested by following the procedure of Example 8. The conversion of the polymerization was found to be 95.5% and the weight average molecular weight of the produced polymer to be 736,000.

EXAMPLE 11

(Copolymerization of styrene and acrylonitrile)

A glass ampoule having an inner volume of 20 ml was charged with 10 ml of a sample solution obtained by dissolving 0.005 mol of 1-cyclohexyl-1-methylethylperoxyisopropyl carbonate as a polymerization initiator and 2 g of t-dodecyl mercaptan as a chain transfer agent in 1 liter of a styrene-acrylonitrile mixture (70:30 by weight ratio), evacuated of the entrapped air, and sealed by fusion. This ampoule was placed in a constant temperature oil bath at 90° C. and left standing therein for five hours to effect polymerization of the styrene-acrylonitrile mixture. Then, the reaction product was removed from the ampoule and dissolved in toluene having hydroquinone dissolved therein. The resultant solution was maintained at 150° C. for one hour to expel the unreacted monomer. The residue of the heat treatment was weighed to find the conversion of the polymerization by calculation. The conversion of the polymerization was found to be 52.4% and the weight average molecular weight of the produced copolymer was found by GPC to be 187,000.

COMPARATIVE EXPERIMENT 2

(Copolymerization of styrene and acrylonitrile)

Copolymerization of styrene and acrylonitrile was carried out by following the procedure of Example 11 while using t-butyl peroxyisopropyl carbonate in place of the peroxide. The conversion of the polymerization was found to be 48.8% and the weight average molecular weight of the produced copolymer to be 203,000.

A comparison of the results of Example 11 with those of Comparative Experiment 2 shows that the peroxide of this invention exhibited higher polymerizing activity and brought about a greater effect in lowering the molecular weight due to the t-dodecyl mercaptan than did the coventional peroxide of Comparative Experiment 2.

EXAMPLE 12

(Copolymerization of α-methyl styrene and acrylonitrile)

A glass ampoule having an inner volume of 20 ml was charged with 10 ml of a sample solution obtained by dissolving 0.05 mol of 1-cyclohexyl-1-methylethylperoxyisopropyl carbonate as a polymerization initiator in 1 liter of an α-methyl styrene-acrylonitrile mixture (70:30 weight ratio), evacuated of the entrapped air, and then sealed by fusion. The ampoule was placed in a constant temperature oil bath at 100° C. and left standing therein for five hours to effect polymerization of the mixture. The product was tested in the same manner as in Example 11. The conversion of the polymerization was found to be 51.5% and the weight average molecular weight of the produced copolymer to be 103,000.

EXAMPLE 13

(Copolymerization of styrene and α-methyl styrene)

A glass ampoule having an inner volume of 20 ml was charged with 10 ml of a sample solution obtained by dissolving 0.05 mol of 1-cyclohexyl-1-methylethylperoxyisopropyl carbonate as a polymerization initiator in 1 liter of a styrene-α-methyl styrene mixture (80:20 weight ratio), evacuated of the entrapped air, and then sealed by fusion. The ampoule was placed in a constant temperature oil bath at 100° C. and left standing for five hours to effect polymerization of the mixture. Then, the product of polymerization was tested in the same manner as in Example 11. As a result, the conversion of the polymerization was found to be 44.8% and the weight average molecular weight of the product to be 80,000.

EXAMPLE 14

(Copolymerization of α-methyl styrene, acrylonitrile, and styrene)

A glass ampoule having an inner volume of 20 ml was charged with 10 ml of a sample solution obtained by dissolving 0.02 mol of 1-cyclohexyl-1-methylethylperoxyisopropyl carbonate as a polymerization initiator in 1 liter of an α-methyl styrene-acrylonitrilestyrene mixture (50:30:20 weight ratio) evacuated of the entrapped air, and then sealed by fusion. The ampoule was placed in a constant temperature oil bath at 100° C., and left standing for five hours to effect polymerization of the mixture. The product consequently obtained was tested in the same manner as in Example 11. The conversion of polymerization was found to be 39.5% and the weight average molecular weight of the product to be 151,000.

(Use as curing agent for unsaturated polyester resin)

EXAMPLE 15

One hundred (100) parts by weight of an unsaturated polyester resin (produced by Nippon Shokubai Kagaku Kogyo Co., Ltd. and marketed under tradename "Epolac G-110AL") and 1 part by weight of 1-cyclohexyl-1-methylethylperoxy-sec-butyl carbonate added thereto as a curing agent were mixed and homogeneously dissolved. A mold was fabricated by opposing two identical glass plates (160×160×5 mm) across a space of 5 mm, with a soft vinyl chloride tube laid along the matched edges of the glass plates and clamps attached to the glass plates to immobilize them relative to each other. The resin added thereto a curing agent as described above was poured in the mold. The mold now filled with the resin was placed with the pouring mouth thereof kept on the upper side in a constant temperature bath at 95° C. and left standing therein for 30 minutes to cure the resin. After the resin was cured and cooled to room temperature. The cold cured resin was removed from the mold and then tested for surface hardness with a Barcole hardness meter. The hardness was found to be 51.

COMPARATIVE EXPERIMENT 3

The same unsaturated polyester resin as used in Example 15 was cured by following the procedure of Example 15 while using 1,1-bis(t-butylperoxy)-3,3,5-trimethylcyclohexane as a curing agent in the place of the peroxide of Example 15. The cured resin was tested for surface hardness in the same manner as in Example 15. The surface hardness was found to be 46.

It is clearly noted from comparison of the results of Example 15 with those of Comparative Experiment 3 that the peroxide of this invention is highly active as compared with the conventional peroxide of Comparative Experiment 3.

(Use as a cross-linking agent for ethylene-vinyl acetate copolymer)

EXAMPLE 16

In a roll mixer, 100 parts by weight of an ethylene-vinyl acetate copolymer containing 25% vinyl acetate, 1 part by weight of stearic acid, and 3 parts by weight of 1,6-bis(1-cyclohexyl-1-methylethylperoxy)-hexamethylene dicarbonate as a cross-linking agent were kneaded at a temperature in the range of 80° to 90° C. The resultant blend was placed in a press and treated therein under a pressure of 150 kg/cm² at a temperature of 150° C. for 40 minutes to cross-link the copolymer. The cross-linked copolymer was analyzed to determine the gel content. The gel content was found to be 92%.

COMPARATIVE EXPERIMENT 4

The same copolymer as used in Example 16 was cross-linked by following the procedure of Example 16 while using t-butyl-peroxybenzoate in the place of the peroxide of Example 16. The produced cross-linked copolymer was analyzed to determine the gel content. The gel content was found to be 83%.

A comparison of the results of Example 16 with those of Comparative Experiment 4 shows that the peroxide of this invention was more highly active than the conventional peroxide of Comparative Experiment 4.

What is claimed is:

1. A 1-cyclohexyl-1-methylethylperoxy carbonate represented by the formula:

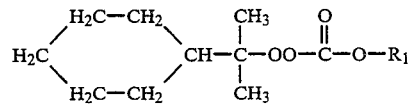

wherein $R_1$ stands for an alkyl group of up to 14 carbon atoms, an aralkyl group of up to 14 carbon atoms, an alkoxyalkyl group of up to 14 carbon atoms, a cycloalkyl group of up to 14 carbon atoms, or an aryl group of up to 14 carbon atoms.

2. A 1-cyclohexyl-1-methylethylperoxy carbonate according to claim 1, wherein $R_1$ is an isopropyl group.

3. A 1-cyclohexyl-1-methylethylperoxy carbonate according to claim 1, wherein $R_1$ is a sec-butyl group.

4. A 1-cyclohexyl-1-methylethylperoxy carbonate according to claim 1, wherein $R_1$ is a 2-ethylhexyl group.

5. A 1-cyclohexyl-1-methylethylperoxy carbonate according to claim 1, wherein $R_1$ is a cyclododecyl group.

6. A 1-cyclohexyl-1-methylethylperoxy carbonate according to claim 1, wherein $R_1$ is a 2-methoxybutyl group.

7. A 1-cyclohexyl-1-methylethylperoxy carbonate according to claim 1, wherein $R_1$ is a p-tolyl group.

8. A polymerization initiator for a vinyl monomer having as an effective component a 1-cyclohexyl-1-methylethylperoxy carbonate set forth in claim 1.

* * * * *